(12) United States Patent
Gidwani et al.

(10) Patent No.: US 6,462,237 B1
(45) Date of Patent: Oct. 8, 2002

(54) CYCLODEXTRIN STABILIZED PHARMACEUTICAL COMPOSITIONS OF BUPROPION HYDROCHLORIDE

(75) Inventors: Suresh Kumar Gidwani, Mumbai (IN); Purushottam Singnurkar, Mumbai (IN); Prashant Kumar Tewari, Mumbai (IN)

(73) Assignee: USV Limited, Mumbai (IN)

( * ) Notice: Subject to any disclaimer, the term of this patent is extended or adjusted under 35 U.S.C. 154(b) by 0 days.

(21) Appl. No.: 09/881,582

(22) Filed: Jun. 14, 2001

(51) Int. Cl.[7] .............................................. C07C 221/00

(52) U.S. Cl. ........................ 564/345; 564/343; 424/488

(58) Field of Search ................................ 564/343, 345; 424/488

(56) References Cited

U.S. PATENT DOCUMENTS 6,383,471 B1 * 5/2002 Chen et al.

* cited by examiner

*Primary Examiner*—Samuel Barts
(74) *Attorney, Agent, or Firm*—Gibbons, Del Deo, Dolan, Griffinger & Vecchione

(57) ABSTRACT

An inclusion complex of bupropion hydrochloride with beta cyclodextrin that stabilizes the bupropion hydrochloride against degradation. A method of preparing an inclusion complex of bupropion hydrochloride with beta cyclodextrin that stabilizes the bupropion hydrochloride against degradation. A novel stabilized sustained-release pharmaceutical composition of bupropion hydrochloride containing an inclusion complex of bupropion hydrochloride with beta cyclodextrin. A method of preparing a novel stabilized sustained-release pharmaceutical composition containing an inclusion complex of bupropion hydrochloride with beta cyclodextrin.

15 Claims, 8 Drawing Sheets

CYCLODEXTRIN STABILIZED PHARMACEUTICAL COMPOSITIONS OF BUPROPION HYDROCHLORIDE

BACKGROUND OF INVENTION

1. Field of Invention

The present invention relates to a stabilized sustained-release pharmaceutical composition of bupropion hydrochloride containing an inclusion complex of bupropion hydrochloride with beta cyclodextrin. The invention also relates to the preparation of a stabilized sustained release pharmaceutical compositions of bupropion hydrochloride containing the inclusion complex of bupropion hydrochloride with beta cyclodextrin.

The invention further relates to a method for preventing the degradation of bupropion hydrochloride by making an inclusion complex with beta cyclodextrin, thus allowing the preparation of acceptable pharmaceutical compositions for sustained release tablets and capsules.

2. Description of Related Art

Bupropion hydrochloride is an antidepressant of the aminoketone class. It is designated as (±)-1-(3-chlorophenyl)-2-[(1,1-dimethylethyl)amino]-1-propane hydrochloride. Bupropion hydrochloride has been shown to decompose in variety of pharmaceutical compositions formulated without the use of stabilizer.

In the present application the term stabilizer means a composition which prevents the decomposition of bupropion hydrochloride.

It has been found that by making an inclusion complex of bupropion hydrochloride with beta cyclodextrin, improved stability of the bupropion hydrochloride results. Accordingly, pharmaceutical compositions of bupropion hydrochloride that contain an inclusion complex of bupropion hydrochloride with beta cyclodextrin will decompose more slowly and maintain their effectiveness for longer periods of time.

It is thus desirable to provide an inclusion complex of bupropion hydrochloride with beta cyclodextrin that improves the stability of the bupropion hydrochloride. It is also desirable to provide a method for preparing an inclusion complex of bupropion hydrochloride with beta cyclodextrin that improves the stability of the bupropion hydrochloride. It is further desirable to provide a stabilized sustained-release pharmaceutical composition of bupropion hydrochloride that contains an inclusion complex of bupropion hydrochloride with beta cyclodextrin. It is still further desirable to provide a method of preparing a stabilized sustained-release pharmaceutical composition of bupropion hydrochloride that contains an inclusion complex of bupropion hydrochloride with beta cyclodextrin.

BRIEF SUMMARY OF THE INVENTION

One aspect of the invention is to provide a method for preparing a composition of an inclusion complex of bupropion hydrochloride with beta cyclodextrin that stabilizes bupropion hydrochloride against degradation, is safe for use as a pharmaceutical composition, is efficient, economical and simple, and which is suitable for manufacture on a commercial scale.

Another aspect of the invention is to provide a method for preparing a stabilized sustained release pharmaceutical composition containing an inclusion complex of bupropion hydrochloride with beta cyclodextrin, which is safe for use as a pharmaceutical composition and stabilizes bupropion hydrochloride against degradation.

DETAILED DESCRIPTION OF THE INVENTION

Figure 1A:
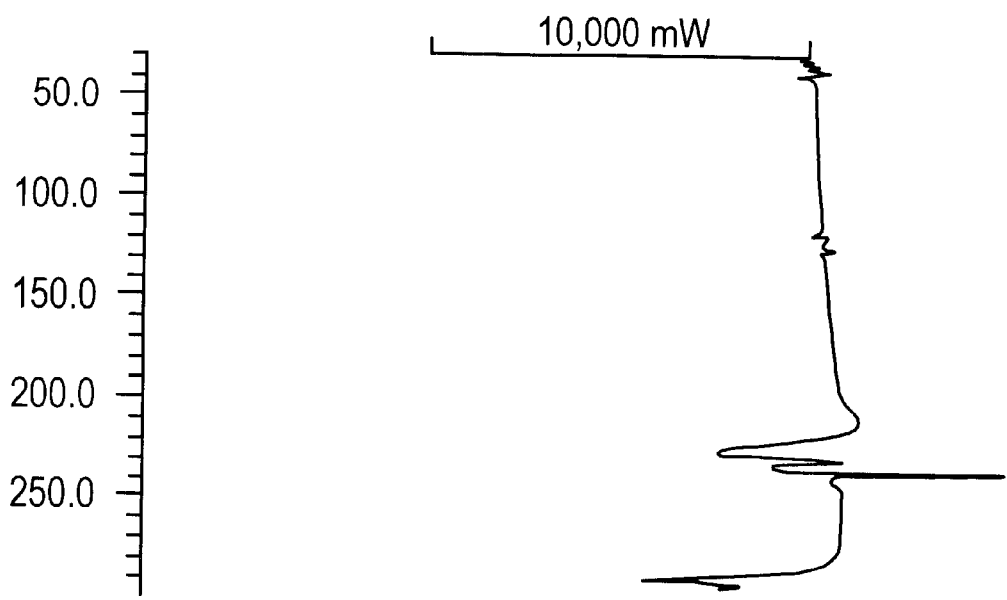
FIG. 1A shows a DSC Thermogram of Bupropion hydrochloride.

The present invention provides a novel inclusion complex of (±)-1-(3-chlorophenyl)-2-[(1,1-dimethylethyl)amino]-1-propane hydrochloride, commonly known as bupropion hydrochloride, of the following Formula 1

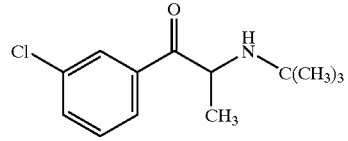

Formula 1 with beta-cyclodextrin, where the molar ratio of bupropion hydrochloride to beta cyclodextrin is 1:(0.25–4). The inclusion complex stabilizes the bupropion hydrochloride against degradation.

The present invention further provides a method for preparing a novel inclusion complex of bupropion hydrochloride with beta cyclodextrin, comprising the steps of:

1. wetting an amount of beta cyclodextrin with a pharmaceutically acceptable solvent such as water, acetone and/or a C1 to C4 aliphatic alcohol and mixtures thereof, at room temperature to form a semisolid mixture;
2. shear mixing the resulting semisolid mixture with bupropion hydrochloride to form an inclusion complex; and 3. drying the shear mixed inclusion complex at 40–80. degrees. C.;

where the molar ratio of bupropion hydrochloride to beta cyclodextrin is 1:(0.25–4.0), and preferably is 1:(0.5–2.0).

In a preferred embodiment, the C1-C4 aliphatic alcohol is selected from the group consisting of isopropyl alcohol, ethanol, and their combinations. The shear mixed inclusion complex may be freeze dried or spray dried or dried by low temperature vacuum evaporation in a fluidized bed dryer or tray dryer. In a preferred embodiment, drying is carried out in a tray dryer at 40–60. degrees. C.

The present invention also provides a novel stabilized sustained release pharmaceutical composition containing the novel inclusion complex of bupropion hydrochloride with beta cyclodextrin, that further contains drug release rate controlling materials selected from a combination of hydroxypropyl methyl cellulose with hydroxypropyl cellulose, sodium carboxymethyl cellulose or stearic acid, the molar ratio of bupropion hydrochloride to beta cyclodextrin being 1:(0.25–4.0). Where a mixture of the release rate controlling materials is employed, the weight ratio of one release rate controlling material to the other is within the range of about 1:0.1 to 0.1:1, and preferably is within the range of about 1:0.3 to 0.3:1.

In a preferred embodiment, the drug release rate controlling materials include hydroxypropyl methyl cellulose with average molecular weight of 20000 to 120000, preferably 86000 to 120000, and with a methoxy degree of substitution ranging from 1.36 to 1.90 and hydroxypropyl molar substitution ranging from 0.18 to 0.25.

Where hydroxypropyl cellulose is employed as a drug release rate controlling material, it preferably has molecular weight in the range of 370000 to 1150000, preferably from 850000 to 1150000. Where sodium carboxymethylcellulose is so employed, it has a molecular weight in the range of 90000 to 700000, preferably from 250000 to 700000, with degree of substitution ranging from 0.65 to 0.95.

The combination of hydroxypropyl methyl cellulose with hydroxypropyl cellulose, sodium carboxymethyl cellulose or stearic acid has been found to effectively control the release rate of bupropion hydrochloride from the pharmaceutical compositions containing the inclusion complex of bupropion hydrochloride with beta cyclodextrin.

The novel stabilized sustained release pharmaceutical composition of the present invention may further contain one or more conventional excipients, such as lactose, microcrystalline cellulose, polyvinyl pyrrolidone, hydroxypropyl methyl cellulose, colloidal silicone dioxide, titanium dioxide, propylene glycol, polyethylene glycol-6000, talc, magnesium stearate and other excipients known in the art.

The novel pharmaceutical compositions according to the present invention can be used to produce oral dosage forms as compressed tablets of any shape, preferably round, or can be formed into compressed compact slugs filled into capsules using modem capsule filling machines. Dosage forms of the novel pharmaceutical composition of the present invention generally contain 25 mg to 500 mg of bupropion hydrochloride, and preferably contain 50 mg, 75 mg, 100 mg, or 150 mg of active ingredient, bupropion hydrochloride.

The present invention also provides a method for preparing a novel stabilized sustained release pharmaceutical composition containing an inclusion complex of bupropion hydrochloride with beta cyclodextrin, and further containing a combination of hydroxypropyl methyl cellulose with hydroxypropyl cellulose, sodium carboxymethyl cellulose or stearic acid, where the molar ratio of bupropion hydrochloride to beta cyclodextrin is 1:(0.25–4.0).

The pharmaceutical compositions of the present invention are prepared by following method:

a) The novel inclusion complex of bupropion hydrochloride with beta cyclodextrin is admixed with the excipients.

b) The mixture is granulated, dried, and milled. Solid dosage forms are prepared such as by compressing the milled granulation to form tablets or caplets. Alternatively capsules may be prepared by placing the compact slugs of milled granulation in, for example, a two part hard gelatin capsule.

c) Solid dosage forms such as tablets may optionally be film coated with aqueous or organic solvent solution of commonly known film coating materials such as hydroxypropyl methyl cellulose, hydroxypropyl cellulose, etc.

The method for preparing the pharmaceutical compositions of the present invention is described in greater detail in the examples that follow.

The in-vitro release rate of bupropion hydrochloride from the sustained release pharmaceutical compositions disclosed herein (whether or not film coated) in 0.1 N HCl up to the first hour and then continued in Phosphate buffer pH 6.8 USP, is preferably as follows:

| Time (Hours) | % Bupropion HCl release |
| --- | --- |
| $1^{st}$ Hour (In 0.1 N HCl) | 20–40% |
| $2^{nd}$ Hour (Phosphate Buffer pH 6.8) | 40–60% |
| $4^{th}$ Hour (Phosphate Buffer pH 6.8) | 60–80% |
| $8^{th}$ Hour (Phosphate Buffer pH 6.8) | NLT 80% |

The stability of the novel sustained release pharmaceutical compositions was tested in accordance with industry standards by storage for four to twelve weeks at various accelerated conditions such as 40. degrees. C. with about 75% relative humidity; and also 50. degrees. C. Sustained release pharmaceutical compositions containing the novel inclusion complex of bupropion hydrochloride with beta cyclodextrin of the present invention stored under these conditions retained at least 98% and at least 95% respectively, of the bupropion hydrochloride in the composition at the time of storage. The amount of bupropion hydrochloride remaining after storage may be determined through HPLC or other standard procedures.

A kinetic degradation study of the novel inclusion complex of bupropion hydrochloride with beta cyclodextrin of the present invention also showed excellent stabilization of bupropion hydrochloride when suspended in water and stored at 50 degrees. C. for four weeks.

Figure 2A:
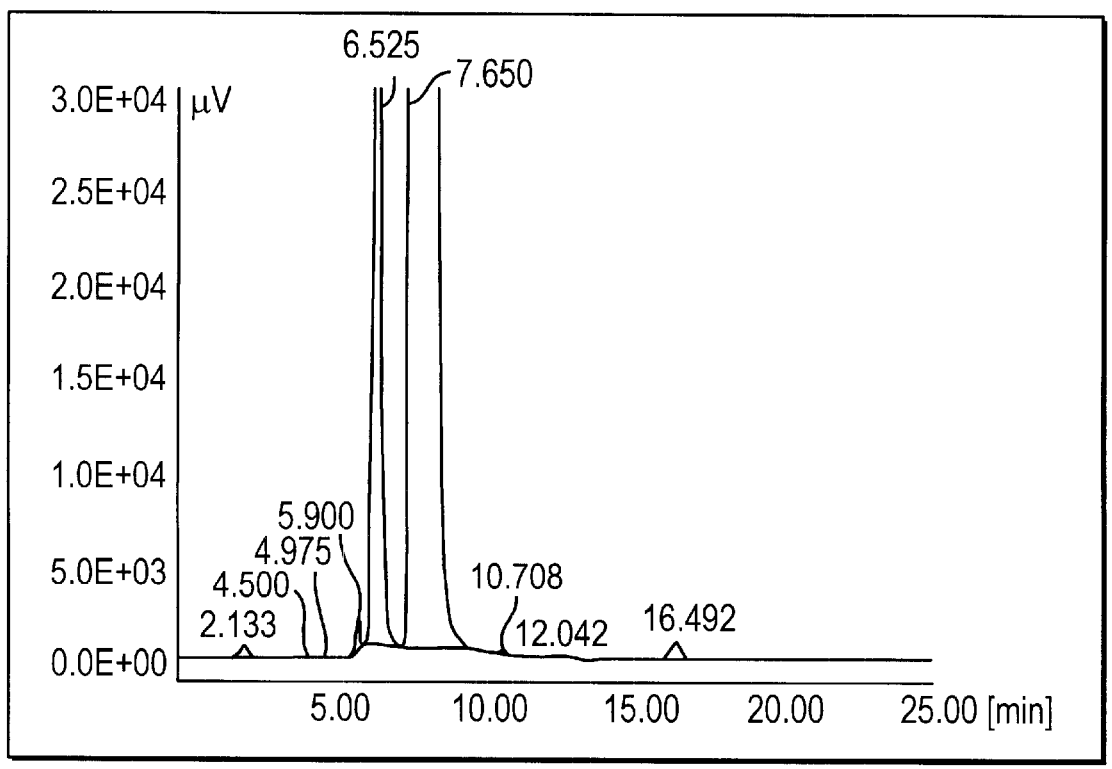
FIG. 2A is an HPLC chromatogram showing the decomposition of bupropion hydrochloride in a sustained release tablet (without an inclusion complex of bupropion hydrochloride with beta cyclodextrin) at 50° C. after 4 weeks. Assay of bupropion hydrochloride=99.998% w/w with respect to standard bupropion hydrochloride.
Figure 2B:
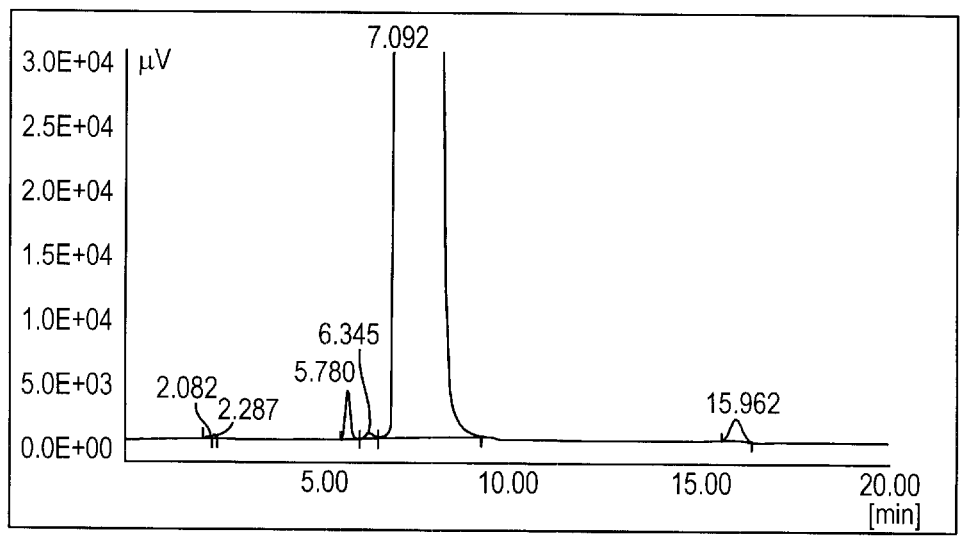
FIG. 2B is an HPLC chromatogram showing the decomposition of bupropion hydrochloride in a sustained release tablet containing an inclusion complex of bupropion hydrochloride with beta cyclodextrin at 50° C. after 4 weeks. Assay of bupropion hydrochloride=99.998% w/w with respect to standard bupropion hydrochloride.
Figure 2C:
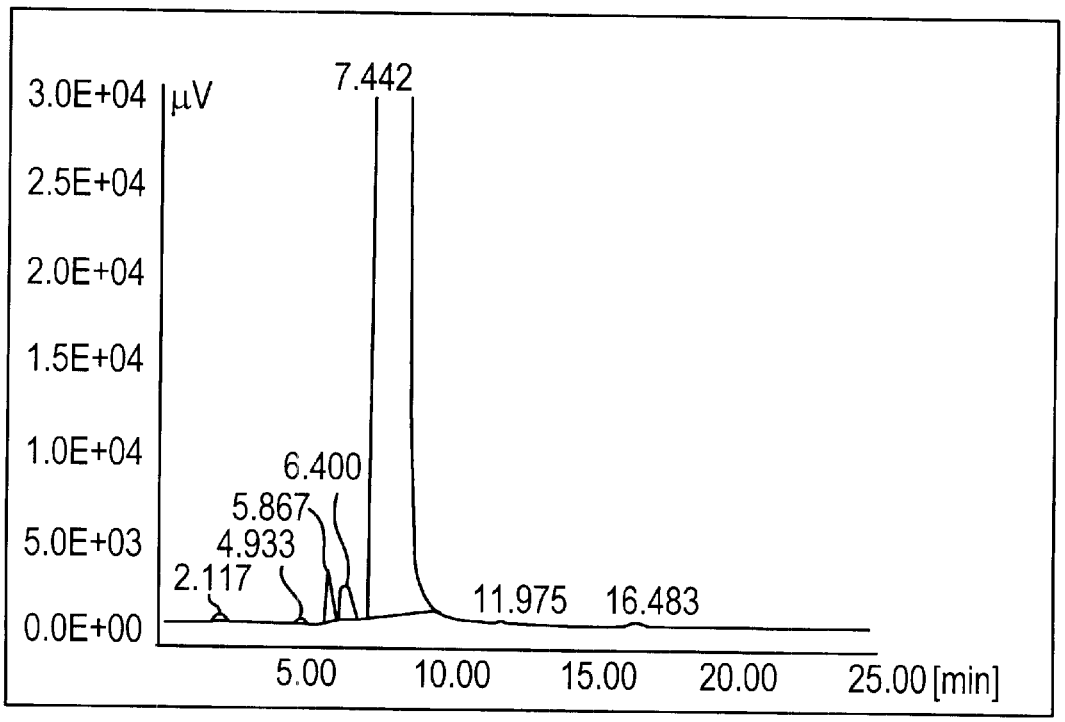
FIG. 2C is an HPLC chromatogram showing the decomposition of bupropion hydrochloride in a sustained release tablet (without an inclusion complex of bupropion hydrochloride with beta cyclodextrin) at 37° C. temperature with 75% relative humidity after 4 weeks. Assay of bupropion hydrochloride=99.998% w/w with respect to standard bupropion hydrochloride.
Figure 2D:
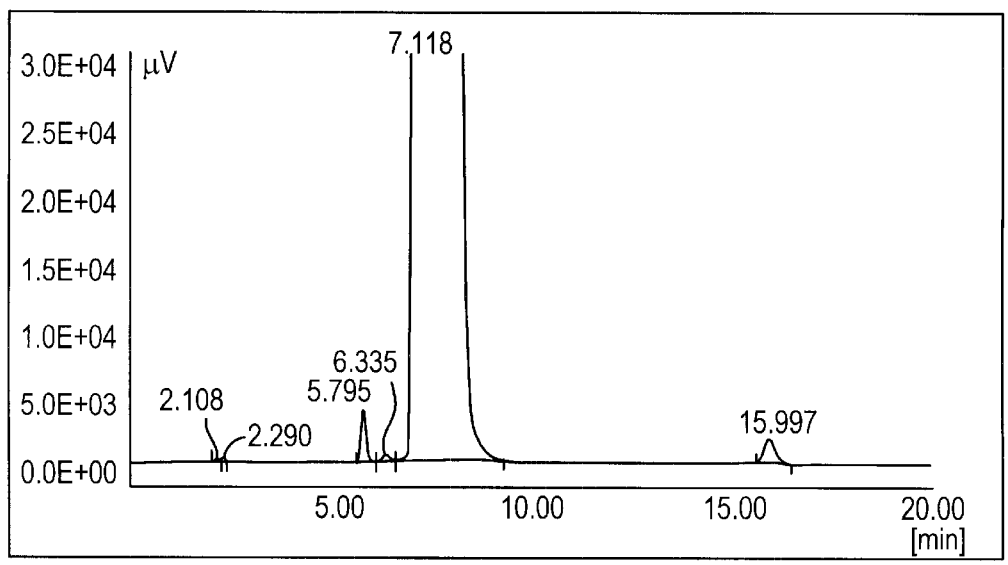
FIG. 2D is an HPLC chromatogram showing the decomposition of bupropion hydrochloride in a sustained release tablet containing an inclusion complex of bupropion hydrochloride with beta cyclodextrin at 37° C. temperature with 75% relative humidity after 4 weeks. Assay of bupropion hydrochloride=99.998% w/w with respect to standard bupropion hydrochloride.

FIG. 2A shows an HPLC chromatogram obtained for a bupropion hydrochloride sustained release tablet without a beta cyclodextrin inclusion complex, containing the same matrix material for a sustained release dosage form as the one for sustained release tablets of bupropion hydrochloride containing the inclusion complex, illustrated by FIG. 2B. One can clearly see the difference in degradation products and assay percentage between the two formulations. The sustained release tablet without the inclusion complex showed the degradation as high as 45% as indicated by FIG. 2A, whereas there is hardly any degradation at 50° C. for over a period of 4 weeks with tablets made with the inclusion complex. FIGS. 2C and 2D further show the HPLC chromatograms illustrating the stability of sustained release tablets not containing the inclusion complex (FIG.

2C) versus those containing inclusion complex (FIG. 2D) at 37° C. with 75% relative humidity. It is clearly again seen that even at low temperature there is sizable degradation, to the extent of 7% over one month period, with a sustained release tablet containing bupropion hydrochloride without the inclusion complex, while hardly any degradation was found with the sustained release bupropion hydrochloride tablets containing the inclusion complex of the present invention.

The preparation of the inclusion complex of the present invention, and of the pharmaceutical compositions of the present invention, is described in greater detail in the following examples. The examples are illustrative, and are not meant to limit the present invention.

EXAMPLE 1

Preparation Bupropion Hydrochloride-beta Cyclodextrin Inclusion Complex (1:0.5 Molar Ratio)

| Ingredients | Weight per Tablet/Capsule | Total quantity per Batch |
|---|---|---|
| Bupropion hydrochloride | 150 mg | 3.000 Kg |
| Beta cyclodextrin | 308 mg | 6.160 Kg |
| Demineralised Water | | 1.000 Kg |

Beta cyclodextrin was wetted in a diasona mixer at a speed of 12 rpm for 15 minutes to get a semisolid mass. To the semisolid mixture, bupropion hydrochloride was added mixed for 1.0 hour. The resulting semisolid mass was dried at 40–60 degrees. C. to get solid inclusion complex of bupropion hydrochloride with beta cyclodextrin.

Accelerated Stability Study

| Period week | % Potency 40° C./75% RH | % Potency 50° C. |
|---|---|---|
| 0 | 99.86 | 99.86 |
| 4 | 99.57 | 97.94 |
| 8 | 99.21 | 96.23 |
| 12 | 98.84 | 95.89 |

Kinetic Degradation Study

A 4.0% w/w solution of bupropion hydrochloride inclusion complex in Demineralised water was made and kept at 50° C. temperature.

| Period weeks | % Potency 50° C. temperature |
|---|---|
| 0 | 99.86 |
| 2 | 97.54 |
| 4 | 95.02 |

EXAMPLE 2

Preparation Bupropion Hydrochloride-beta Cyclodextrin Inclusion Complex (1:0.5 Molar Ratio)

| Ingredients | Weight per Tablet/Capsule | Total quantity per Batch |
|---|---|---|
| Bupropion hydrochloride | 150 mg | 3.000 Kg |
| Beta cyclodextrin | 308 mg | 6.160 Kg |
| Ethanol + Water (1:1) mixture | | 1.000 Kg |

Beta cyclodextrin was wetted in a diasona mixer at a speed of 12 rpm for 15 minutes to get a semisolid mass. To the semisolid mixture, bupropion hydrochloride was added mixed for 1.0 hour. The resulting semisolid mass was dried at 40–60 degrees. C. to get a solid inclusion complex of bupropion hydrochloride with beta cyclodextrin.

Accelerated Stability Study

| Period week | % Potency 40° C./75% RH | % Potency 50° C. |
|---|---|---|
| 0 | 100.12 | 100.12 |
| 4 | 99.97 | 98.82 |
| 8 | 99.65 | 97.39 |
| 12 | 99.27 | 95.94 |

Kinetic Degradation Study

A 4.0% w/w solution of bupropion hydrochloride inclusion complex in Demineralised water was made and kept at 50° C. temperature.

| Period weeks | % Potency 50° C. temperature |
|---|---|
| 0 | 99.86 |
| 2 | 97.66 |
| 4 | 95.18 |

EXAMPLE 3

Preparation Bupropion Hydrochloride-beta Cyclodextrin Inclusion Complex (1:0.5 Molar Ratio)

| Ingredients | Weight per Tablet/Capsule | Total quantity per Batch |
|---|---|---|
| Bupropion hydrochloride | 150 mg | 3.000 Kg |
| Beta cyclodextrin | 308 mg | 6.160 Kg |
| Ethanol | | 1.000 Kg |

Beta cyclodextrin was wetted in a diasona mixer at a speed of 12 rpm for 15 minutes to get a semisolid mass. To the semisolid mixture, bupropion hydrochloride was added mixed for 1.0 hour. The resulting semisolid mass was dried at 40–60 degrees. C. to get solid inclusion complex of bupropion hydrochloride with beta cyclodextrin.

Accelerated Stability Study

| Period week | % Potency 40° C./75% RH | % Potency 50° C. |
|---|---|---|
| 0 | 100.47 | 100.47 |
| 4 | 100.19 | 98.73 |
| 8 | 99.88 | 97.05 |
| 12 | 99.67 | 95.4 |

Kinetic Degradation Study

A 4.0% w/w solution of bupropion hydrochloride inclusion complex in Demineralised water was made and kept at 50° C. temperature.

| Period weeks | % Potency 50° C. temperature |
|---|---|
| 0 | 100.47 |
| 2 | 98.06 |
| 4 | 95.52 |

EXAMPLE 4

Preparation Bupropion Hydrochloride-beta Cyclodextrin Inclusion Complex (1:1 Molar Ratio)

| Ingredients | Weight per Tablet/Capsule | Total quantity per Batch |
|---|---|---|
| Bupropion hydrochloride | 150 mg | 3.000 Kg |
| Beta cyclodextrin | 616 mg | 12.320 Kg |
| Demineralised Water | | 2.000 Kg |

Beta cyclodextrin was wetted in a diasona mixer at a speed of 12 rpm for 15 minutes to get a semisolid mass. To the semisolid mixture, bupropion hydrochloride was added mixed for 1.0 hour. The resulting semisolid mass was dried at 40–60 degrees. C. to get solid inclusion complex of bupropion hydrochloride with beta cyclodextrin.

Accelerated Stability Study

| Period week | % Potency 40° C./75% RH | % Potency 50° C. |
|---|---|---|
| 0 | 100.05 | 100.05 |
| 4 | 99.91 | 98.68 |
| 8 | 99.54 | 97.05 |
| 12 | 99.33 | 95.57 |

Kinetic Degradation Study

A 4.0% w/w solution of bupropion hydrochloride inclusion complex in Demineralised water was made and kept at 50° C. temperature.

| Period weeks | % Potency 50° C. temperature |
|---|---|
| 0 | 100.05 |
| 2 | 97.85 |
| 4 | 95.84 |

EXAMPLE 5

Preparation Bupropion Hydrochloride-beta Cyclodextrin Inclusion Complex (1:1 Molar Ratio)

| Ingredients | Weight per Tablet/Capsule | Total quantity per Batch |
|---|---|---|
| Bupropion hydrochloride | 150 mg | 3.000 Kg |
| Beta cyclodextrin | 616 mg | 12.320 Kg |
| Ethanol + Water (1:1) mixture | | 2.000 Kg |

Beta cyclodextrin was wetted in a diasona mixer at a speed of 12 rpm for 15 minutes to get a semisolid mass. To the semisolid mixture, bupropion hydrochloride was added mixed for 1.0 hour in suitable mixers/kneader known in art. The resulting semisolid mass was dried at 40–60 degrees. C. to get solid inclusion complex of bupropion hydrochloride with beta cyclodextrin.

Accelerated Stability Study

| Period week | % Potency 40° C./75% RH | % Potency 50° C. |
|---|---|---|
| 0 | 99.91 | 99.91 |
| 4 | 99.65 | 98.51 |
| 8 | 99.37 | 91.16 |
| 12 | 99.07 | 95.64 |

Kinetic Degradation Study

A 4.0% w/w solution of bupropion hydrochloride inclusion complex in Demineralised water was made and kept at 50° C. temperature.

| Period weeks | % Potency 50° C. temperature |
|---|---|
| 0 | 99.91 |
| 2 | 97.71 |
| 4 | 95.56 |

EXAMPLE 6

Preparation Bupropion Hydrochloride-beta Cyclodextrin Inclusion Complex (1:2 Molar Ratio)

| Ingredients | Weight per Tablet/Capsule | Total quantity per Batch |
|---|---|---|
| Bupropion hydrochloride | 150 mg | 3.000 Kg |
| Beta cyclodextrin | 1232 mg | 24.464 Kg |
| Ethanol + Water (1:1) mixture | | |

Beta cyclodextrin was wetted in a diasona mixer at a speed of 12 rpm for 15 minutes to get a semisolid mass. To the semisolid mixture, bupropion hydrochloride was added mixed for 1.0 hour. The resulting semisolid mass was dried at 40–60 degrees. C. to get solid inclusion complex of bupropion hydrochloride with beta cyclodextrin.

Accelerated stability study:

| Period week | % Potency 40° C./75% RH | % Potency 50° C. |
|---|---|---|
| 0 | 101.02 | 101.02 |
| 4 | 100.76 | 99.72 |
| 8 | 100.55 | 98.22 |
| 12 | 100.32 | 96.74 |

Kinetic Degradation Study

A 4.0% w/w solution of bupropion hydrochloride inclusion complex in Demineralised water was made and kept at 50° C. temperature.

| Period weeks | % Potency 50° C. temperature |
|---|---|
| 0 | 101.02 |
| 2 | 98.82 |
| 4 | 96.39 |

EXAMPLE 7

Sustained Release Tablet

| Ingredients | Weight per Tablet | Total quantity per Batch |
|---|---|---|
| Bupropion hydrochloride-beta cyclodextrin inclusion complex of Example 1. | 458 mg (Equivalent to 150 mg bupropion hydrochloride) | 4580 gm |
| Hydroxypropyl cellulose | 10 mg | 100 gm |
| Hydroxypropyl methyl cellulose | 40 mg | 400 gm |
| Povidone K-30 | 15 mg | 150 gm |
| Aerosil ® | 1.5 mg | 15 gm |
| Magnesium stearate | 1.5 mg | 15 gm |

Bupropion hydrochloride-beta cyclodextrin complex, hydroxypropyl cellulose and hydroxypropyl methyl cellulose were sifted through #40 mesh screen.

The screened ingredients were transferred to a mixer granulator and mixed for 10 minutes. The mixed material was granulated with solution of povidone k-30 in isopropyl alcohol.

The granulated material was dried in the tray oven at 40° C. and then milled to get required size granules.

Aerosil® and magnesium stearate were sifted through #60 mesh screen to milled materials. The screened and milled material was blended in a double cone blender for 15 minutes. The blend material was compressed into tablets with compression weight of about 526 mg per tablet.

The compressed tablet cores (5260 gm) were aqueous film coated using 948.8 gm of the following coating formulation.

| Ingredients | Weight per Tablet | Total quantity per Batch |
|---|---|---|
| Hydroxypropyl methyl cellulose | 4 mg | 40 gm |
| Titanium dioxide | 1.6 mg | 16 gm |
| Propylene glycol | 0.32 mg | 3.2 gm |
| Polyethylene glycol | 0.32 mg | 3.2 gm |
| Talc | 2.4 mg | 24 gm |
| Isopropyl alcohol | 21.52 mg | 215.2 gm |
| Demineralised water | 64.6 mg | 646 gm |
| Red iron oxide | 012 mg | 1.2 gm |

The tablet cores were coated using Accela Coata tablet coating machine.

Bed Temperature:38–40° C.

Inlet Temperature:60° C.

Pan speed during warming:1–2 RPM.

Pan speed during coating:4–5 RPM.

Spray Rate:40–45 ml per minute.

Accelerated stability study:

| Period week | % Potency 40° C./75% RH | % Potency 50° C. |
|---|---|---|
| 0 | 100.56 | 100.56 |
| 4 | 100.35 | 99.35 |
| 8 | 100.11 | 98.02 |
| 12 | 99.92 | 96.89 |

The in-vitro release rate of bupropion hydrochloride form the sustained release tablets disclosed (whether or not film coated) herein in 0.1 N HCl up to first hour and then continued in Phosphate buffer pH 6.8 USP, is preferably as follows

| Time (Hours) | % Bupropion HCl release |
|---|---|
| $1^{st}$ Hour (In 0.1N HCl) | 27–29% |
| $2^{nd}$ Hour (Phosphate Buffer pH 6.8) | 44–47% |
| $4^{th}$ Hour (Phosphate Buffer pH 6.8) | 64–68% |
| $8^{th}$ Hour (Phosphate Buffer pH 6.8) | 89–93% |

EXAMPLE 8

Sustained Release Tablet

| Ingredients | Weight per Tablet | Total quantity per Batch |
|---|---|---|
| Bupropion hydrochloride-beta cyclodextrin inclusion complex of Example 1. | 458 mg (Equivalent to 150 mg bupropion hydrochloride | 4580 gm |
| Carboxymethyl cellulose sodium | 10 mg | 100 gm |
| Hydroxypropyl methyl cellulose | 40 mg | 400 gm |
| Povidone K-30 | 15 mg | 150 gm |
| Aerosil ® | 1.5 mg | 15 gm |
| Magnesium stearate | 1.5 mg | 15 gm |

Bupropion hydrochloride-beta cyclodextrin complex, carboxymethyl cellulose sodium and hydroxypropyl methyl cellulose were sifted through #40 mesh screen.

The screened ingredients were transferred to a mixer granulator and mixed for 10 minutes. The mixed material was granulated with solution of povidone k-30 in isopropyl alcohol.

The granulated material was dried in the tray oven at 40° C. and then milled to get required size granules.

Aerosil® and magnesium stearate were sifted through #60 mesh screen to milled materials. The screened and milled material was blended in a double cone blender for 15 minutes. The blend material was compressed into tablets with compression weight of about 526 mg per tablet.

The compressed tablet cores (5260 gm) were aqueous film coated using 948.8 gm of the following coating formulation.

| Ingredients | Weight per Tablet | Total quantity per Batch |
|---|---|---|
| Hydroxypropyl methyl cellulose | 4 mg | 40 gm |
| Titanium dioxide | 1.6 mg | 16 gm |
| Propylene glycol | 0.32 mg | 3.2 gm |
| Polyethylene glycol | 0.32 mg | 3.2 gm |
| Talc | 2.4 mg | 24 gm |
| Isopropyl alcohol | 21.52 mg | 215.2 gm |
| Demineralised water | 64.6 mg | 646 gm |
| Red iron oxide | 012 mg | 1.2 gm |

The tablet cores were coated using Accela Coata tablet coating machine.

Bed Temperature: 38–40° C.

Inlet Temperature: 60° C.

Pan speed during warming: 1–2 RPM.

Pan speed during coating: 4–5 RPM.

Spray Rate: 40–45 ml per minute.

Accelerated stability study

| Period week | % Potency 40° C./75% RH | % Potency 50° C. |
|---|---|---|
| 0 | 99.95 | 99.95 |
| 4 | 99.73 | 98.69 |
| 8 | 99.52 | 97.43 |
| 12 | 99.29 | 96.25 |

The in-vitro release rate of bupropion hydrochloride form the sustained release tablets disclosed (whether or not film coated) herein in 0.1 HCl up to first hour and then continued in Phosphate buffer pH 6.8 USP, is preferably as follows

| Time (Hours) | % Bupropion HCl release |
|---|---|
| $1^{st}$ Hour (In 0.1N HCl) | 25–27% |
| $2^{nd}$ Hour (Phosphate Buffer pH 6.8) | 43–48% |
| $4^{th}$ Hour (Phosphate Buffer pH 6.8) | 63–65% |
| $8^{th}$ Hour (Phosphate Buffer pH 6.8) | 88–92% |

EXAMPLE 9

Sustained Release Tablet

| Ingredients | Weight per Tablet | Total quantity per Batch |
|---|---|---|
| Bupropion hydrochloride-beta cyclodextrin inclusion complex of Example 1. | 458 mg (Equivalent to 150 mg bupropion hydrochloride | 4580 gm |
| Stearic acid | 10 mg | 100 gm |
| Hydroxypropyl methyl cellulose | 32 mg | 320 gm |
| Povidone K-30 | 15 mg | 150 gm |
| Aerosil ® | 1.5 mg | 15 gm |
| Magnesium stearate | 1.5 mg | 15 gm |

Bupropion hydrochloride-beta cyclodextrin complex, stearic acid and hydroxypropyl methyl cellulose were sifted through #40 mesh screen.

The screened ingredients were transferred to a mixer granulator and mixed for 10 minutes. The mixed material was granulated with solution of povidone k-30 in isopropyl alcohol.

The granulated material was dried in the tray oven at 40° C. and then milled to get required size granules.

Aerosil® and magnesium stearate were sifted through #60 mesh screen to milled materials. The screened and milled material was blended in a double cone blender for 15 minutes. The blend material was compressed into tablets with compression weight of about 518 mg per tablet.

The compressed tablet cores (5180 gm) were aqueous film coated using 948.8 gm of the following coating formulation.

| Ingredients | Weight per Tablet | Total quantity per Batch |
|---|---|---|
| Hydroxypropyl methyl cellulose | 4 mg | 40 gm |
| Titanium dioxide | 1.6 mg | 16 gm |
| Propylene glycol | 0.32 mg | 3.2 gm |
| Polyethylene glycol | 0.32 mg | 3.2 gm |
| Talc | 2.4 mg | 24 gm |
| Isopropyl alcohol | 21.52 mg | 215.2 gm |
| Demineralised water | 64.6 mg | 646 gm |
| Red iron oxide | 012 mg | 1.2 gm |

The tablet cores were coated using Accela Coata tablet coating machine.

Bed Temperature:38–40° C.
Inlet Temperature:60° C.
Pan speed during warming:1–2 RPM.
Pan speed during coating:4–5 RPM.
Spray Rate:40–45 ml per minute.

Accelerated stability study:

| Period week | % Potency 40° C./75% RH | % Potency 50° C. |
|---|---|---|
| 0 | 100.46 | 100.46 |
| 4 | 100.23 | 99.13 |
| 8 | 100.02 | 97.84 |
| 12 | 99.87 | 96.5 |

The in-vitro release rate of bupropion hydrochloride form the sustained release tablets disclosed (whether or not film coated) herein in 0.1 N HCl up to first hour and then continued in Phosphate buffer pH 6.8 USP, is preferably as follows

| Time (Hours) | % Bupropion HCl release |
|---|---|
| 1st Hour (In 0.1N HCl) | 28–33% |
| 2nd Hour (Phosphate Buffer pH 6.8) | 50–57% |
| 4th Hour (Phosphate Buffer pH 6.8) | 68–72% |
| 8th Hour (Phosphate Buffer pH 6.8) | 85–92% |

EXAMPLE 10

Sustained Release Tablet

| Ingredients | Weight per Tablet | Total quantity per Batch |
|---|---|---|
| Bupropion hydrochloride-beta cyclodextrin inclusion complex of Example 1. | 458 mg (Equivalent to 150 mg bupropion hydrochloride | 4580 gm |
| Hydroxypropyl cellulose | 30 mg | 300 gm |
| Hydroxypropyl methyl cellulose | 25 mg | 250 gm |
| Povidone K-30 | 15 mg | 150 gm |

-continued

| Ingredients | Weight per Tablet | Total quantity per Batch |
|---|---|---|
| Aerosil ® | 1.5 mg | 15 gm |
| Magnesium stearate | 1.5 mg | 15 gm |

Bupropion hydrochloride-beta cyclodextrin complex, hydroxypropyl cellulose and hydroxypropyl methyl cellulose were sifted through #40 mesh screen.

The screened ingredients were transferred to a mixer granulator and mixed for 10 minutes. The mixed material was granulated with solution of povidone k-30 in isopropyl alcohol.

The granulated material was dried in the tray oven at 40° C. and then milled to get required size granules.

Aerosil® and magnesium stearate were sifted through #60 mesh screen to milled materials. The screened and milled material was blended in a double cone blender for 15 minutes. The blend material was compressed into tablets with compression weight of about 531 mg per tablet.

The compressed tablet cores (5310 gm) were aqueous film coated using 948.8 gm of the following coating formulation.

| Ingredients | Weight per Tablet | Total quantity per Batch |
|---|---|---|
| Hydroxypropyl methyl cellulose | 4 mg | 40 gm |
| Titanium dioxide | 1.6 mg | 16 gm |
| Propylene glycol | 0.32 mg | 3.2 gm |
| Polyethylene glycol | 0.32 mg | 3.2 gm |
| Talc | 2.4 mg | 24 gm |
| Isopropyl alcohol | 21.52 mg | 215.2 gm |
| Demineralised water | 64.6 mg | 646 gm |
| Red iron oxide | 012 mg | 1.2 gm |

The tablet cores were coated using Accela Coata tablet coating machine.

Bed Temperature:38–40° C.
Inlet Temperature:60° C.
Pan speed during warming:1–2 RPM.
Pan speed during coating:4–5 RPM.
Spray Rate:40–45 ml per minute.

Accelerated stability study:

| Period week | % Potency 40° C./75% RH | % Potency 50° C. |
|---|---|---|
| 0 | 101.2 | 101.2 |
| 4 | 100.97 | 99.85 |
| 8 | 100.68 | 98.49 |
| 12 | 100.36 | 97.19 |

In-vitro release rate of bupropion hydrochloride form the sustained release tablets disclosed (whether or not film coated) herein in 0.1 N HCl up to first hour and then continued in Phosphate buffer pH 6.8 USP, is preferably as follows

| Time (Hours) | % Bupropion HCl release |
|---|---|
| 1st Hour (In 0.1N HCl) | 27–28% |
| 2nd Hour (Phosphate Buffer pH 6.8) | 44–50% |
| 4th Hour (Phosphate Buffer pH 6.8) | 64–66% |
| 8th Hour (Phosphate Buffer pH 6.8) | 92–94% |

| Time (Hours) | % Bupropion HCl release |
|---|---|
| 1st Hour (In 0.1N HCl) | 27–29% |
| 2nd Hour (Phosphate Buffer pH 6.8) | 44–47% |
| 4th Hour (Phosphate Buffer pH 6.8) | 64–68% |
| 8th Hour (Phosphate Buffer pH 6.8) | 89–93% |

EXAMPLE 11

Sustained Release Capsule

| Ingredients | Weight per Tablet | Total quantity per Batch |
|---|---|---|
| Bupropion hydrochloride-beta cyclodextrin inclusion complex of Example 1. | 458 mg (Equivalent to 150 mg bupropion hydrochloride | 4580 gm |
| Hydroxypropyl cellulose | 10 mg | 100 gm |
| Hydroxypropyl methyl cellulose | 40 mg | 400 gm |
| Povidone K-30 | 15 mg | 150 gm |
| Aerosil ® | 1.5 mg | 15 gm |
| Magnesium stearate | 1.5 mg | 15 gm |

Bupropion hydrochloride-beta cyclodextrin complex, hydroxypropyl cellulose and hydroxypropyl methyl cellulose were sifted through #40 mesh screen.

The screened ingredients were transferred to a mixer granulator and mixed for 10 minutes. The mixed material was granulated with solution of povidone k-30 in isopropyl alcohol.

The granulated material was dried in the tray oven at 40° C. and then milled to get required size granules.

Aerosil® and magnesium stearate were sifted through #60 mesh screen to milled materials. The screened and milled material was blended in a double cone blender for 15 minutes. The blend material was compressed into compact slugs with weight of about 526 mg and filled in size 0 capsule.

| Accelerated stability study: | | |
|---|---|---|
| Period week | % Potency 40° C./75% RH | % Potency 50° C. |
| 0 | 99.99 | 99.99 |
| 4 | 99.74 | 98.66 |
| 8 | 99.52 | 97.42 |
| 12 | 99.24 | 96.105 |

The in-vitro release rate of bupropion hydrochloride form the sustained release tablets disclosed (whether or not film coated) herein in 0.1 N HCl up to first hour and then continued in Phosphate buffer pH 6.8 USP, is preferably as follows

EXAMPLE 12

Sustained Release Tablet

| Ingredients | Weight per Tablet | Total quantity per Batch |
|---|---|---|
| Bupropion hydrochloride-beta cyclodextrin inclusion complex of Example 4. | 766 mg (Equivalent to 150 mg bupropion hydrochloride | 7660 gm |
| Hydroxypropyl cellulose | 20 mg | 200 gm |
| Hydroxypropyl methyl cellulose | 80 mg | 800 gm |
| Povidone K-30 | 20 mg | 200 gm |
| Aerosil ® | 2 mg | 20 gm |
| Magnesium stearate | 2 mg | 20 gm |

Bupropion hydrochloride-beta cyclodextrin complex, hydroxypropyl cellulose and hydroxypropyl methyl cellulose were sifted through #40 mesh screen.

The screened ingredients were transferred to a mixer granulator and mixed for 10 minutes. The mixed material was granulated with solution of povidone k-30 in isopropyl alcohol.

The granulated material was dried in the tray oven at 40° C. and then milled to get required size granules.

Aerosil® and magnesium stearate were sifted through #60 mesh screen to milled materials. The screened and milled material was blended in a double cone blender for 15 minutes. The blend material was compressed into tablets with compression weight of about 890 mg per tablet.

The compressed tablet cores (8900 gm) were aqueous film coated using 1422.9 gm of the following coating formulation.

| Ingredients | Weight per Tablet | Total quantity per Batch |
|---|---|---|
| Hydroxypropyl methyl cellulose | 6 mg | 60 gm |
| Titanium dioxide | 2.4 mg | 24 gm |
| Propylene glycol | 0.48 mg | 4.8 gm |
| Polyethylene glycol | 0.48 mg | 4.8 gm |
| Talc | 3.6 mg | 36 gm |
| Isopropyl alcohol | 32.28 mg | 322.8 gm |
| Demineralised water | 96.9 mg | 969 gm |
| Red iron oxide | 0.15 mg | 1.5 gm |

The tablet cores were coated using Accela Coata tablet coating machine.

Bed Temperature: 38–40° C.

Inlet Temperature: 60° C.

Pan speed during warming:1–2 RPM.
Pan speed during coating:4–5 RPM.
Spray Rate 40–45 ml per minute.
Accelerated Stability Study

| Period week | % Potency 40° C./75% RH | % Potency 50° C. |
|---|---|---|
| 0 | 99.97 | 99.97 |
| 4 | 99.71 | 98.72 |
| 8 | 99.42 | 97.41 |
| 12 | 99.13 | 96.09 |

In-vitro release rate of bupropion hydrochloride form the sustained release tablets disclosed (whether or not film coated) herein in 0.1 N HCl up to first hour and then continued in Phosphate buffer pH 6.8 USP, is preferably as follows

| Time (Hours) | % Bupropion HCl release |
|---|---|
| 1$^{st}$ Hour (In 0.1N HCl) | 29–31% |
| 2$^{nd}$ Hour (Phosphate Buffer pH 6.8) | 46–50% |
| 4$^{th}$ Hour (Phosphate Buffer pH 6.8) | 68–70% |
| 8$^{th}$ Hour (Phosphate Buffer pH 6.8) | 90–93% |

Figure 1B:
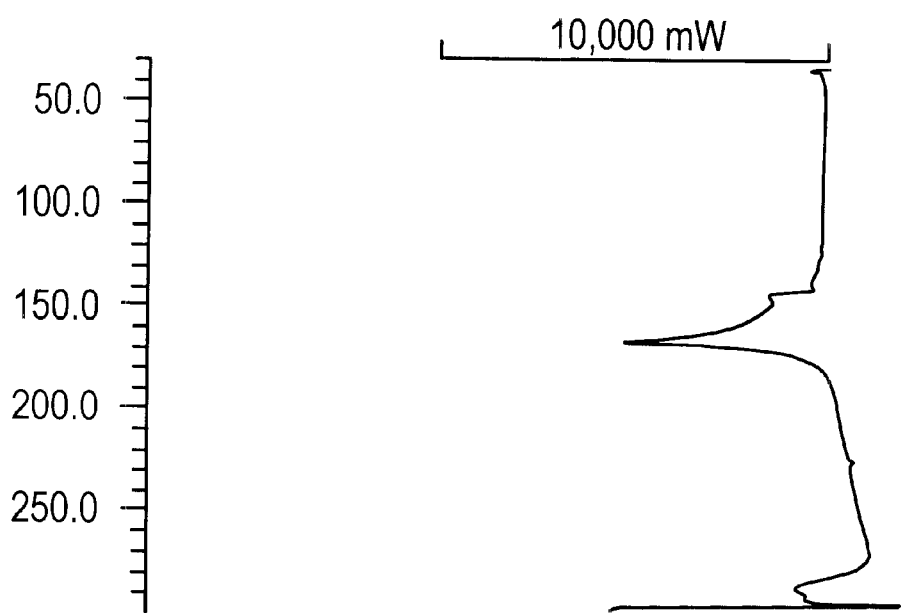
FIG. 1B shows a DSC Thermogram of Beta cyclodextrin.
Figure 1C:
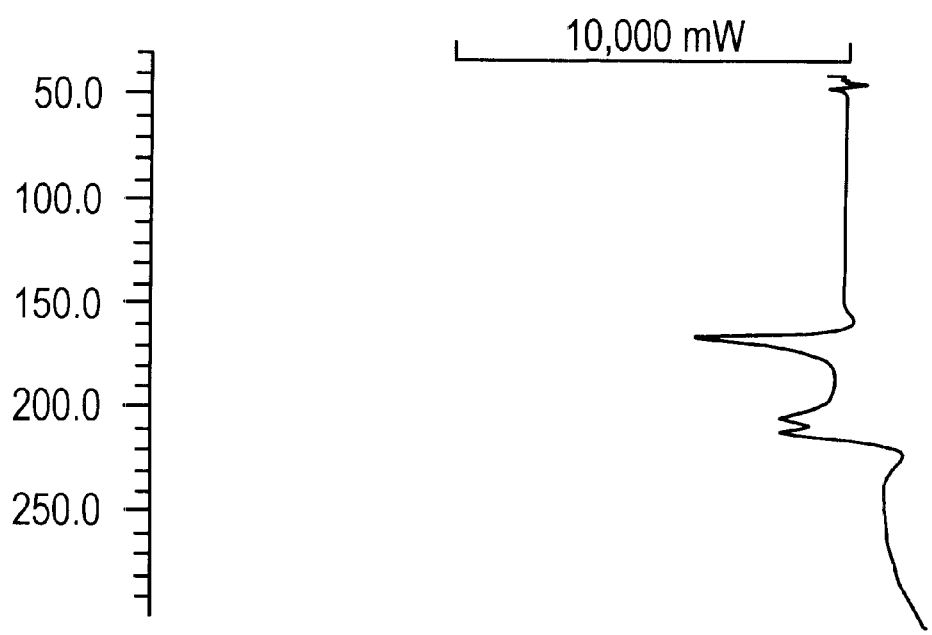
FIG. 1C shows a DSC Thermogram of a physical mixture of bupropion hydrochloride with beta cyclodextrin (1:1).
Figure 1D:
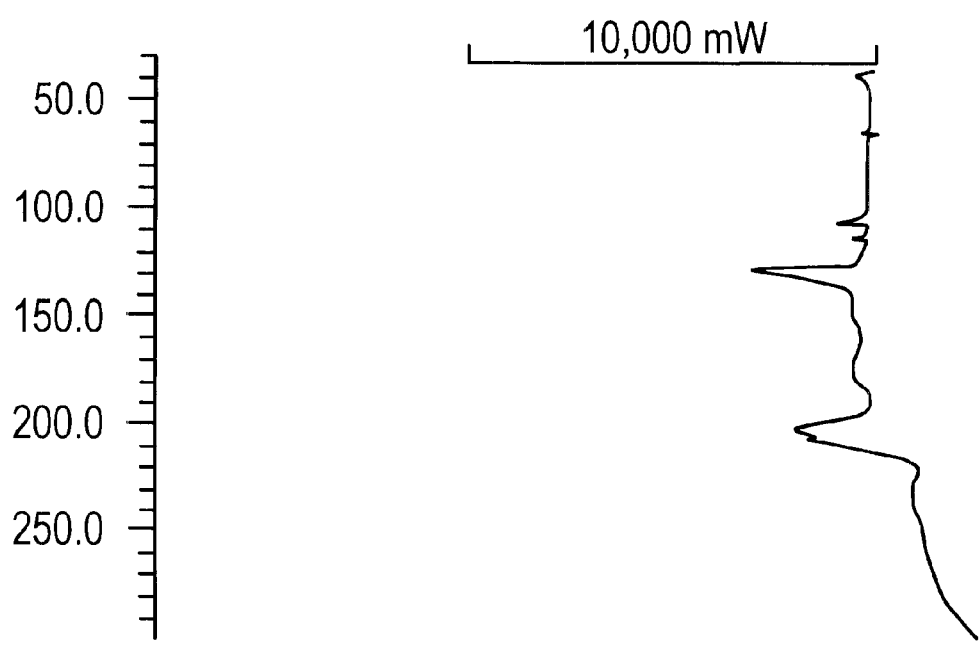
FIG. 1D shows a DSC Thermogram of an inclusion complex of bupropion hydrochloride with beta cyclodextrin.

The inclusion complex of the present invention is characterized as follows:

Thermograms of bupropion hydrochloride, beta cyclodextrin, a physical mixture of bupropion hydrochloride and beta cyclodextrin 1:1 and the bupropion hydrochloride-beta cyclodextrin inclusion complex of the invention are as shown in FIGS. 1A, 1B, 1C, and 1D respectively. The peak at 224° C. in FIG. 1A was due to the melting of bupropion hydrochloride. FIG. 1B shows an endothermic peak at 168° C. corresponding to beta cyclodextrin. The physical mixture showed endothermic peaks of both bupropion hydrochloride at 205.9° C. and beta cyclodextrin at 159.5° C. as in FIG. 1C. The inclusion complex showed an endothermic peak of cyclodextrin sifted to 126° C. while endothermic peak of the bupropion hydrochloride remained at 209° C. as in FIG. 1D.

The weights of the inclusion complex and physical mixture were strictly identical. Normally, when an acidic or basic drug is taken without its salts, it has been observed that the drug's endothermic peak merges with the endothermic peak of beta cyclodextrin. In this case, however, a substantial shift in endothermic peak of beta cyclodextrin in the inclusion complex is seen, but not in the case of the physical mixture. This is seen as a proof of inclusion complex formation. The formation of inclusion complex is further evidenced by 2D NOESY NMR spectra using Bruker 600 Hz FTNMR.

While the invention has been described with respect to certain specific embodiments, it will be appreciated that many modifications and changes may be made by those skilled in the art without departing from the invention. It is intended, therefore, by the appended claims to cover all such modifications and changes as may fall within the true spirit and scope of the invention.

We claim:

1. An inclusion complex of bupropion hydrochloride that is(±)-1-(3-chlorophenyl)-2-[(1,1-dimethylethyl)amino]-1-propane hydrochloride, of the following formula

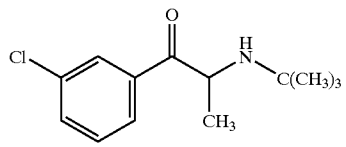

with beta-cyclodextrin, where bupropion hydrochloride and beta cyclodextrin are present in a molar ratio of 1:(0.25–4).

2. The inclusion complex of claim 1, wherein the molar ratio of bupropion hydrochloride to beta cyclodextrin is 1:(0.5–2).

3. A method for preparing an inclusion complex of bupropion hydrochloride with beta cyclodextrin comprising:
   a) wetting an amount of beta cyclodextrin with one or more pharmaceutically acceptable solvents selected from a group consisting of water, acetone, a C1 to C4 aliphatic alcohol and mixtures thereof at room temperature to form a semisolid mixture;
   b) shear mixing the semisolid mixture with bupropion hydrochloride to form an inclusion complex; and
   c) drying the shear mixed inclusion complex at 40–60 degrees C. to form the inclusion complex of bupropion hydrochloride with beta cyclodextrin;
   wherein bupropion hydrochloride and beta cyclodextrin are present in a molar ratio of 1:(0.25–2.0).

4. The method of claim 3, wherein the C1 to C4 aliphatic alcohol is selected from a group consisting of ethanol and isopropyl alcohol.

5. The method of claim 3, wherein the molar ratio of bupropion to betacyclodextrin is 1: (1–2).

6. A method for preparing an inclusion complex of bupropion hydrochloride with beta-cyclodextrin, comprising:
   a) wetting an amount of beta cyclodextrin with one or more pharmaceutically acceptable solvents to form a semisolid mixture, the beta cyclodextrin and the solvents being present in a weight ratio (w/w) of 6.16:1;
   b) admixing an amount of bupropion hydrochloride to the semisolid mixture to form an admixed inclusion complex; and
   c) drying the admixed inclusion complex at 40–60 degrees C. to form a solid inclusion complex of bupropion hydrochloride with beta cyclodextrin,
   wherein bupropion hydrochloride and beta cyclodextrin are present in a molar ratio of 1:(0.5–2).

7. A stabilized sustained release formulation of an inclusion complex of bupropion hydrochloride with beta-cyclodextrin in combination with pharmaceutically acceptable excipients, wherein bupropion hydrochloride and beta-cyclodextrin are present in a molar ratio of 1:(0.25–1).

8. The stabilized sustained release formulation of claim 7, wherein the pharmaceutically acceptable excipients are drug release rate controlling materials comprising a combination of a first excipient consisting of hydroxypropyl methyl cellulose with a second excipient selected from a group consisting of hydroxypropyl cellulose, sodium carboxymethyl cellulose and stearic acid, where the first excipient and the second excipient are in a weight ratio of about 1:0.1 to 0.1:1.

9. The stabilized sustained release formulation of claim 7, wherein bupropion hydrochloride and beta-cyclodextrin are present in a molar ratio of 1:(0.5–2).

10. The stabilized sustained release formulation of claim 7, wherein bupropion hydrochloride is present in an amount selected from 50 mg, 75 mg, 100 mg and 150 mg.

11. A method for the preparation of a stabilized sustained release formulation containing a bupropion hydrochloride-beta cyclodextrin inclusion complex, comprising:

a) sifting together an amount of bupropion hydrochloride-beta cyclodextrin inclusion complex and an amount of one or more drug release rate controlling materials, through a screen;
b) mixing the sifted and screened inclusion complex and drug release rate controlling materials to form a mixed material;
c) granulating the mixed material with alcohol;
d) drying the granulated material in an oven;
e) milling the dried granulated material to obtain granules;
f) sifting a first mixture of pharmaceutically acceptable excipients through a mesh screen and adding the sifted excipients to the milled granules;
g) blending the sifted excipients and the milled granules to form a blended material;
h) compressing the blended material into oral dosage forms, the oral dosage forms having a compression weight of approximately 500–900 mg per form; and
i) coating the oral dosage forms with an aqueous second mixture of pharmaceutically acceptable excipients, wherein bupropion hydrochloride and beta cyclodextrin are present in a molar ratio of 1: (0.5–1).

12. The method of claim 11, wherein the drug release rate controlling materials comprise a combination of a first substance consisting of hydroxypropyl methyl cellulose with a second substance selected from a group consisting of hydroxypropyl cellulose, sodium carboxymethyl cellulose and stearic acid.

13. The method of claim 11, wherein the first mixture of pharmaceutically acceptable excipients comprises Aerosil® and magnesium stearate.

14. The method of claim 11, wherein the aqueous second mixture of pharmaceutically acceptable excipients consists of an aqueous mixture of hydroxypropylmethyl cellulose, titanium dioxide, propylene glycol, polyethylene glycol, talc, isopropyl alcohol, red iron oxide, and demineralized water, with the hydroxypropylmethyl cellulose, titanium dioxide, propylene glycol, polyethylene glycol, talc, isopropyl alcohol, red iron oxide, and demineralized water being present in a weight ratio of 40:16:3.2:3.2:24:215.2:1.2:646.

15. The method of claim 4, wherein the molar ratio of bupropion ride to betacyclodextrin is 1: (1–2).

* * * * *